United States Patent [19]

Christidis

[11] Patent Number: 4,978,784
[45] Date of Patent: Dec. 18, 1990

[54] PROCESS FOR INDUSTRIAL MANUFACTURE OF SODIUM PARAHYDROXYMANDELATE

[75] Inventor: Yani Christidis, Paris, France

[73] Assignee: Societe Francaise Hoechst, Puteaux, France

[21] Appl. No.: 426,352

[22] Filed: Oct. 25, 1989

[30] Foreign Application Priority Data

Nov. 8, 1988 [FR] France ................ 88 14.575

[51] Int. Cl.$^5$ .................. C07C 59/48; C07C 59/52
[52] U.S. Cl. .................................................. 562/470
[58] Field of Search ........................................ 562/470

[56] References Cited

U.S. PATENT DOCUMENTS 4,408,070 10/1983 Schouteeten et al. .

FOREIGN PATENT DOCUMENTS 0024181 8/1980 European Pat. Off. .
2427322 12/1979 France .
54-61142 5/1979 Japan .
102537 8/1980 Japan .
WO/00404 2/1981 PCT Int'l Appl. .

OTHER PUBLICATIONS

Houben-Weyl Methoden Der Organischen Chemie, 4th edition, 1976, Georg Thieme Verlag, Stuttgart, p. 1036, paragraph 5, lines 1-3.

Primary Examiner—Paul J. Killos
Attorney, Agent, or Firm—Browdy and Neimark

[57] ABSTRACT

This process is characterized by the fact that glyoxylic acid in aqueous solution is reacted with an excess of phenol in the presence of a tertiary amine, insoluble or slightly soluble in water and liquid at ambient temperature, in particular tributylamine or triisooctylamine, then the parahydroxymandelic acid thus obtained is salified with sodium hydroxide in aqueous solution.

The reaction of the glyoxylic acid with phenol is carried out at a temperature between 15° C. and 80° C.

8 Claims, No Drawings

PROCESS FOR INDUSTRIAL MANUFACTURE OF SODIUM PARAHYDROXYMANDELATE

The present invention relates to a new process for industrial manufacture of sodium parahydroxymandelate.

Pure crystallized sodium parahydroxymandelate, anhydrous or with one molecule of water, is described in the literature (French Patent Nos. 2,426,669, 2,427,322) and it enables parahydroxymandelic acid to be obtained very easily and with excellent yields. This acid, as well as its ammonium salts or alkali metal salts or alkaline-earth metal salts, are valuable raw materials for obtaining in particular various synthesis intermediates such as parahydroxybenzaldehyde and parahydroxyphenyl-acetic acid, which have important outlets in the pharmaceutical industry.

Numerous methods are known for the preparation of parahydroxymandelic acid as well as its salts, and more particularly the reaction of glyoxylic acid with phenol, hot, in an aqueous medium and in the presence of an alkali metal hydroxide (French Patent Nos. 2,427,322, 2,440,350, 2,456,722, 2,495,137 and 2,426,669). This condensation cannot be regioselective and in addition to parahydroxymandelic acid, relatively large quantities of orthohydroxymandelic acid and 4-hydroxy-1,3-benzene-diglycolic acid are formed. Furthermore, this condensation necessitates working in a dilute aqueous medium, with large excesses of phenol and sodium hydroxide which involve costly treatments for isolating the product sought and for recycling, or possibly destruction of the mother liquors.

In order to avoid all these inconveniences, the Applicant has now discovered that it is possible to obtain advantageously pure crystallized sodium parahydroxymandelate with a good yield, avoiding, during the condensation of glyoxylic acid with phenol, the presence of a strong mineral base, by reacting the glyoxylic acid, in aqueous solution, with an excess of phenol, in the presence of only a tertiary amine alone, insoluble or very slightly soluble in water and liquid at ambient temperature, then by salifying the parahydroxymandelic acid thus obtained with an aqueous solution of sodium hydroxide.

According to the process of the invention, the condensation of the glyoxylic acid with an excess of phenol, in the presence of a tertiary amine which is liquid at ambient temperature and insoluble or very slightly soluble in water, is carried out at a temperature between 15° C. and 80° C., advantageously between 40° C. and 60° C.

As tertiary amines liquid at ambient temperature and insoluble or slightly soluble in water, there can be cited tributylamine, trioctylamine, triisooctylamine or their mixtures, as well as various commercial mixtures of tertiary amines, such as those marketed by the Applicant under the name HOSTAREX ®, seeing that they offer the required conditions quoted previously. In the present case, slightly soluble in water signifies that at 20° C. the aqueous solubility is less than or equal to that of tributylamine.

Glyoxylic acid is used in aqueous solution, advantageously in aqueous solution at concentrations greater than 50% by weight and preferably in aqueous solution at 65±2% by weight.

According to the process of the invention, an excess of 2 to 8 moles of phenol and 1 to 5 moles of tertiary amine per mole of glyoxylic acid employed is used, then at the end of the reaction, an aqueous solution of sodium hydroxide is introduced so as to salify the parahydroxymandelic acid formed.

At the end of the reaction, the crystallized sodium parahydroxymandelate is isolated with one molecule of water by means known per se. Advantageously, at the end of the reaction, an aqueous solution of sodium hydroxide is introduced into the reaction mixture, then after decanting the two-phase system obtained, the sodium parahydroxymandelate crystallized with one molecule of water is isolated from the possibly concentrated aqueous phase, because it loses its water of crystallization by drying at 110° C., so providing anhydrous crystallized sodium parahydroxymandelate.

The following examples are given as an illustration of the invention and are in no way limitative.

EXAMPLE 1

The following are mixed at 20° C., under agitation and in an inert atmosphere:

69.5 g (0.375 mole) of tributylamine,
188.2 g (2 moles) of phenol, then over 30 minutes the following is introduced into this agitated solution:
28.48 g of an aqueous solution of glyoxylic acid at 65% by weight, that is, 0.25 mole.

The emulsion thus obtained is then heated to 40° C. over 30 minutes, then to 60° C. over 30 minutes, and finally it is left for 60 minutes at this temperature before being cooled to 45° C. At this temperature, 203 g of an aqueous solution of sodium hydroxide at 8.87% by weight, or 0.45 mole, is introduced, followed by decanting. The organic phase (232.4 g) is retained for recycling and the aqueous phase (253 g) is washed three times with 50 ml of 1,1-dimethyl-1-methoxy propane, which enables 12.65 g (0.134 mole) of phenol to be recovered. At this stage, the analysis of a sample by chromatography in liquid phase reveals that the aqueous phase contains, in a salified state, 15% by weight (35.3 g) of parahydroxymandelic acid, or a yield of 84%, 2.1% by weight (4.9 g) of ortho-hydroxymandelic acid and 0.1% (0.23 g) of 4-hydroxy-1,3-benzene-diglycolic acid, and that it is free from phenol and tributylamine. The aqueous phase is then concentrated hot under vacuum, to about 130 g, then it is left to crystallize at about 5° C. and finally it is filtered. The crystals recovered are washed with an iced mixture of water and isopropanol 1-1 (v/v), then dried under vacuum at 40° C. to constant weight. Thus 38.5 g (0.185 mole) of sodium parahydroxy-mandelate crystallized with one molecule of water is isolated, that is a yield of 74% of the theoretical amounted calculated relative to the glyoxylic acid used.

The organic phase is recycled directly in a second identical operation after the phenol used up in the previous operation has been added to it, that is 35.5 g (0.377 mole).

Thus once again 38.4 g (0.185 mole) of sodium parahydroxy-mandelate crystallized with one molecule of water is obtained.

EXAMPLE 2

The following are mixed at 20° C., under agitation and in an inert atmosphere:

132.6 g (0.375 mole) of triisooctylamine,
141.15 g (1.5 mole) of phenol, then over 345 minutes, at 20°±3° C., the following is introduced into this agitated solution:

37 g of an aqueous solution of glyoxylic acid at 50% by weight, that is, 0.25 mole.

When the introduction is finished, 200 g of an aqueous solution of sodium hydroxide at 5% by weight, that is, 0.25 mole, is introduced at ambient temperature, then the two-phase reaction medium obtained is decanted. The organic phase (253.5 g) is retained for recycling, and the aqueous phase (251.6 g) is analysed by chromatography in liquid phase.

These analyses indicate the presence of 13.3% (33.41 g, 0.199 mole) of parahydroxymandelic acid, 1.1% (2.76 g, 16.4 moles) of orthohydroxymandelic acid, 2.3% (5.78 g, 61.4 mmoles) of phenol and 0.2% (0.5 g, 2 mmoles) of 4-hydroxy-1,3-benzenediglycolic acid.

At this stage, the yield is 79.6% of the theoretical amount calculated relative to the glyoxylic acid used. The aqueous phase is then treated as in Example 1 and 36.4 g (0.175 mole) of pure sodium parahydroxymandelate crystallized with one molecule of water is thus isolated, that is a yield of 70% of the theoretical amount calculated relative to the glyoxylic acid used.

It goes without saying that the present invention has been described only as a purely explanatory and in no way limitative example, and that any modification, in particular as regards equivalents, could be made to it without exceeding its scope.

I claim:

1. Process for the industrial manufacture of sodium parahydroxymandelate, consisting essentially of
    (1) reacting glyoxylic acid in aqueous solution with an excess of phenol in the presence of a tertiary amine, said tertiary amine being insoluble or slightly soluble in water and liquid at ambient temperature, and
    (2) then salifying the parahydroxymandelic acid thus obtained with sodium hydroxide in aqueous solution.

2. Process according to claim 1, wherein the reaction of the glyoxylic acid in aqueous solution with an excess of phenol is carried out at a temperature between 15° C. and 80° C.

3. Process according to claim 2, wherein this reaction is carried out at a temperature of 20°±3° C.

4. Process according to claim 1 wherein the tertiary amine is tributylamine.

5. Process according to claim 1 wherein the tertiary amine is triisooctylamine.

6. A process according to claim 2 wherein the tertiary amine is selected from the group consisting of tributylamine and triisooctylamine.

7. A process according to claim 3 wherein the tertiary amine is selected from the group consisting of tributylamine and triisooctylamine.

8. A process for the manufacture of sodium parahydroxymandelate in two steps, comprising
    condensing glyoxylic acid with phenol at a temperature of 15°–80° C. in the absence of a strong mineral base and in the presence of a tertiary amine, said tertiary amine being insoluble or slightly soluble in water and being liquid at ambient temperature, and said glyoxylic acid being in aqueous solution at a concentration greater than 50% by weight, to produce parahydroxymandelic acid, and
    adding sodium hydroxide in aqueous solution to said parahydroxymandelic acid to form sodium parahydroxymandelate.

* * * * *